(12) United States Patent
Franco et al.

(10) Patent No.: US 8,445,428 B2
(45) Date of Patent: May 21, 2013

(54) PLANT DERIVED ANTIBIOTIC PEPTIDE RICH IN GLYCINE

(75) Inventors: Octavio Franco, Asa Norte (BR); Patricia Barbosa Pelegrini, Asa Norte (BR); Carlos Bloch Junior, Plano Piloto (BR); Luciano Paulino Silva, Plano Piloto (BR)

(73) Assignees: Uniao Brasiliense de Educacao e Cultura—UBEC, Taguantinga-DF (BR); Empresa Brasileira de Pesquisa Agropercuaria—EMBRAPA, Brasilia-DF (BR)

( * ) Notice: Subject to any disclaimer, the term of this patent is extended or adjusted under 35 U.S.C. 154(b) by 234 days.

(21) Appl. No.: 12/521,716

(22) PCT Filed: Jan. 2, 2008

(86) PCT No.: PCT/BR2008/000001
§ 371 (c)(1),
(2), (4) Date: Apr. 13, 2011

(87) PCT Pub. No.: WO2008/080208
PCT Pub. Date: Jul. 10, 2008

(65) Prior Publication Data
US 2011/0190197 A1    Aug. 4, 2011

(30) Foreign Application Priority Data
Dec. 29, 2006 (BR) ..................................... 0605658

(51) Int. Cl.
*A61K 38/00* (2006.01)
(52) U.S. Cl.
USPC ........................................................ 514/2.3

(58) Field of Classification Search
None
See application file for complete search history.

(56) References Cited

PUBLICATIONS

Egorov. et al.,Peptides 26 (Apr. 2005) p. 2066.*
Tomika, M. et al., US005304663A, Apr. 1994, cols. 3-4.*
Egorov et al., Peptides, 2005, 26, 2064-2073.*
Egorov TA, Odintsova TI, Pukhalsky VA, Grishin EV. Diversity of wheat anti-microbial peptides. Peptides. Nov. 2005;26(11):2064-73 Epub Apr. 19, 2005.
Pelegrini PB, Noronha EF, Muniz MA, Vasconcelos IM, Chiarello MD, Oliveira JT, Franco OL. "An antifungal peptide from passion fruit (*Passiflora edulis*) seeds with similarities to 2S albumin proteins." Biochim Biophys Acta. Jun. 2006;1764(6):1141-6.
Arima H, Danno G. "Isolation of Antimicrobial compounds from guava (*Psidium quajava* L. ) and their structural elucidation." Biosci Biotechnol Biochem. Aug. 2002;66(8):1727-30.

* cited by examiner

*Primary Examiner* — Marcela M Cordero Garcia
*Assistant Examiner* — Kaipeen Yang
(74) *Attorney, Agent, or Firm* — Arent Fox LLP

(57) ABSTRACT

The present invention relates to a novel peptide extracted from guava (*Psidium guajava*) seeds, that provides bactericide activity, Preferentially against Gram-negative bacteria which are known to cause urinary, hospital, and intestinal tract infections (*Proteus* sp. And *Klebsiella* sp.). The peptide, that has the amino acid sequence RESPSSRMEC YEQAERYGYG GYGGGRYGGG YGSGRGQPVG QGVERSHDDN RNQPR, belongs to the class of glycine rich proteins and has approximately 5 kDa of molecular weight. The invention also relates to antibiotic compositions for human, veterinary and plant treatments. Alternatively, the peptide, or a functionally similar derivative, subjects of the present invention, can be used for transforming organisms aiming pathogen resistance, other adaptive advantages, as well as various properties, specially for plants and animals.

5 Claims, 6 Drawing Sheets

N- RESPSSRMECYEQAERYGYGGYGGGRYGGGYGSGRGQPVGQGVERSHDDNRNQPR- C    SEQ ID NO:1

```
                 10         20         30         40         50         60         70         80         90        100
                 ....|....|....|....|....|....|....|....|....|....|....|....|....|....|....|....|....|....|....|....|
PgAMP1           RE------------SPSSRMECYEQ-A----ERYGYG-GYGG-----RYGG-YGS-----GRG----QPVGQG----VERSHDDNR----  SEQ ID NO: 1
Zea mays         RELTEANGSGLRWMVRPAGEPGLKDEKW----FGGRYKHGGGYGNM--QPGYGG--GGMSQP---GYGG-GGMSQPGYGGG----YRRHHPGGG----  SEQ ID NO: 3
Physcomitrella patens RETGRSRGPG----FVTFADENSMNEAIRD--MNGKELDGRNITVN--QAQSREGGSGG------GGGGY------------------MNRGGGGG---  SEQ ID NO: 4
Brassica napus   RETGRSRGFG----FVTFKDERSMKDAIDE--MNGKELDGRNITVN--EAQSRGGGGGG------RGGG-----YGG-RGGG----YGGGGG-------  SEQ ID NO: 5
Solanum tuberosum RETGRSRGFG----FVTFKDEQAMRDAIEG--MNGQDLDGRNITVN--EAQSRGGGGGGG----RGGG-----YGGG RREGG---GGG YGGGGG----  SEQ ID NO: 6
Medicago sativa  RETGRSRGFG----FVTFANEKSMNDVIEA--MNGQDLDGRNITVN--QAQSRGSG-GGG-----GG-----------------RGGG----------  SEQ ID NO: 7
Rumex obtusifolius RETGRSRGFG----FVTFSSEQAMRDAIEG--MNGQDLDGRNITVN--EAQSRGSGGGGG---Y-RGGGG---CYGG-RREGG---YNR-GGGGG----  SEQ ID NO: 8
Euphorbia esula  RETGRSRGFG----FVTFMNEKSMRDAIQG--MMSQELDGRNITVN--EAQSRGSG-GG-----GGGG Y SRGSGGGGNGG----YSRGGGGGG YGGG  SEQ ID NO: 9
Oryza sativa     --------------KPTGRSGVEDQRWSGAHGG YGYGGG YGGG YGHPGYGGG YGGG YGHP---GYGGG YGGG YGGG YGCG----YGHPSHSGG---  SEQ ID NO: 10

110        120        130
                 ....|....|....|....|....|...
PgAMP1           N-------QPR-----------------                                SEQ ID NO: 1
Zea mays         YG------SGQGGPGC-GCGGG YGGG N-                              SEQ ID NO: 3
Physcomitrella patens YG------GCG-----------------                          SEQ ID NO: 4
Brassica napus   YG--DRRGGG Y-----GSGGG RGGG-                                SEQ ID NO: 5
Solanum tuberosum YGGG RREGGGGG - YSGGGGG YGGG-                              SEQ ID NO: 6
Medicago sativa  YG-----GGGG-----------------                                SEQ ID NO: 7
Rumex obtusifolius YGGGGG YGGGGG YGGGGGG YGGG-                                SEQ ID NO: 8
Euphorbia esula  GRREGG YG------GGGG Y-------NSRSGG-                         SEQ ID NO: 9
Oryza sativa     YG------GGGG YGGGGG YGGSHGGGWP                              SEQ ID NO: 10
```

Figure 3B

SEQUENCE LISTING

```
<160> NUMBER OF SEQ ID NOS: 10

<210> SEQ ID NO 1
<211> LENGTH: 55
<212> TYPE: PRT
<213> ORGANISM: Psidium guajava

<400> SEQUENCE: 1

Arg Glu Ser Pro Ser Ser Arg Met Glu Cys Tyr Glu Gln Ala Glu Arg
1               5                   10                  15

Tyr Gly Tyr Gly Gly Tyr Gly Gly Gly Arg Tyr Gly Gly Gly Tyr Gly
            20                  25                  30

Ser Gly Arg Gly Gln Pro Val Gly Gln Gly Val Glu Arg Ser His Asp
        35                  40                  45

Asp Asn Arg Asn Gln Pro Arg
    50                  55

<210> SEQ ID NO 2
<211> LENGTH: 55
<212> TYPE: PRT
<213> ORGANISM: Psidium guajava

<400> SEQUENCE: 2

Arg Glu Ser Pro Ser Ser Arg Met Glu Cys Tyr Glu Gln Ala Glu Arg
1               5                   10                  15

Tyr Gly Tyr Gly Gly Tyr Gly Gly Gly Arg Tyr Gly Gly Gly Tyr Gly
            20                  25                  30

Ser Gly Arg Gly Gln Pro Val Gly Gln Gly Val Glu Arg Ser His Asp
        35                  40                  45

Asp Asn Arg Asn Gln Pro Arg
    50                  55

<210> SEQ ID NO 3
<211> LENGTH: 98
```

```
<212> TYPE: PRT
<213> ORGANISM: Zea mays

<400> SEQUENCE: 3

Arg Glu Leu Thr Glu Ala Asn Gly Ser Gly Leu Lys Asn Asn Val Lys
1               5                   10                  15

Pro Ala Gly Glu Pro Gly Leu Lys Asp Glu Lys Trp Phe Gly Gly Arg
            20                  25                  30

Tyr Lys His Gly Gly Tyr Gly Asn Asn Gln Pro Gly Tyr Gly Gly
        35                  40                  45

Gly Gly Asn Ser Gln Pro Gly Tyr Gly Gly Gly Asn Ser Gln Pro
        50                  55                  60

Gly Tyr Gly Gly Tyr Lys Arg His His Pro Gly Gly Tyr Gly
65                  70                  75                  80

Ser Gly Gln Gly Gly Pro Gly Cys Gly Cys Gly Gly Tyr Gly Gly
            85                  90                  95

Gly Asn

<210> SEQ ID NO 4
<211> LENGTH: 71
<212> TYPE: PRT
<213> ORGANISM: Physcomittrela patens

<400> SEQUENCE: 4

Arg Glu Thr Gly Arg Ser Arg Gly Phe Gly Phe Val Thr Phe Ala Asp
1               5                   10                  15

Glu Asn Ser Met Asn Glu Ala Ile Lys Asp Met Asn Gly Lys Glu Leu
            20                  25                  30

Asp Gly Arg Asn Ile Thr Val Asn Gln Ala Gln Ser Arg Gly Gly Gly
        35                  40                  45

Ser Gly Gly Gly Gly Gly Gly Tyr Asn Arg Gln Gly Gly Gly
        50                  55                  60

Gly Gly Tyr Gly Gly Gly Gly
65                  70

<210> SEQ ID NO 5
<211> LENGTH: 93
<212> TYPE: PRT
<213> ORGANISM: Brassica napus

<400> SEQUENCE: 5

Arg Glu Thr Gly Arg Ser Arg Gly Phe Gly Phe Val Thr Phe Lys Asp
1               5                   10                  15

Glu Lys Ser Met Lys Asp Ala Ile Asp Glu Met Asn Gly Lys Glu Leu
            20                  25                  30

Asp Gly Arg Thr Ile Thr Val Asn Glu Ala Gln Ser Arg Gly Gly Gly
        35                  40                  45

Gly Gly Gly Gly Arg Gly Gly Gly Tyr Gly Arg Gly Gly Gly
        50                  55                  60

Gly Tyr Gly Gly Gly Gly Tyr Gly Asp Arg Arg Gly Gly Gly
65                  70                  75                  80

Gly Tyr Gly Ser Gly Gly Gly Arg Gly Gly Gly
            85                  90

<210> SEQ ID NO 6
<211> LENGTH: 100
<212> TYPE: PRT
<213> ORGANISM: Solanum tuberosum
```

-continued

<400> SEQUENCE: 6

Arg Glu Thr Gly Arg Ser Arg Gly Phe Gly Phe Val Thr Phe Lys Asp
1               5                   10                  15

Glu Gln Ala Met Arg Asp Ala Ile Glu Gly Met Asn Gly Gln Asp Leu
            20                  25                  30

Asp Gly Arg Asn Ile Thr Val Asn Glu Ala Gln Ser Arg Gly Gly Gly
        35                  40                  45

Gly Gly Gly Gly Gly Arg Gly Gly Gly Gly Tyr Gly Gly Gly Arg Arg
    50                  55                  60

Glu Gly Gly Gly Gly Tyr Gly Gly Gly Gly Tyr Gly Gly
65                  70                  75                  80

Arg Arg Glu Gly Gly Gly Gly Gly Tyr Ser Gly Gly Gly Gly
                85                  90                  95

Tyr Gly Gly Gly
            100

<210> SEQ ID NO 7
<211> LENGTH: 65
<212> TYPE: PRT
<213> ORGANISM: Medicago sativa

<400> SEQUENCE: 7

Arg Glu Thr Gly Arg Ser Arg Gly Phe Gly Phe Val Thr Phe Ala Asn
1               5                   10                  15

Glu Lys Ser Met Asn Asp Val Ile Glu Ala Met Asn Gly Gln Asp Leu
            20                  25                  30

Asp Gly Arg Asn Ile Thr Val Asn Gln Ala Gln Ser Arg Gly Ser Gly
        35                  40                  45

Gly Gly Gly Gly Arg Gly Gly Gly Tyr Gly Gly Gly Gly
    50                  55                  60

Gly
65

<210> SEQ ID NO 8
<211> LENGTH: 102
<212> TYPE: PRT
<213> ORGANISM: Rumex obtusifolius

<400> SEQUENCE: 8

Arg Glu Thr Gly Arg Ser Arg Gly Phe Gly Phe Val Thr Phe Ser Ser
1               5                   10                  15

Glu Gln Ala Met Arg Asp Ala Ile Glu Gly Met Asn Gly Gln Asp Leu
            20                  25                  30

Asp Gly Arg Asn Ile Thr Val Asn Glu Ala Gln Ser Arg Gly Ser Gly
        35                  40                  45

Gly Gly Gly Gly Tyr Arg Gly Gly Gly Gly Gly Tyr Gly Gly
    50                  55                  60

Arg Arg Glu Gly Gly Tyr Asn Arg Gly Gly Gly Tyr Gly Gly
65                  70                  75                  80

Gly Gly Gly Gly Tyr Gly Gly Gly Gly Tyr Gly Gly Gly
                85                  90                  95

Gly Gly Tyr Gly Gly Gly
            100

<210> SEQ ID NO 9
<211> LENGTH: 102
<212> TYPE: PRT
<213> ORGANISM: Euphorbia osula

```
<400> SEQUENCE: 9

Arg Glu Thr Gly Arg Ser Arg Gly Phe Gly Phe Val Thr Phe Asn Asn
1               5                   10                  15

Glu Lys Ser Met Arg Asp Ala Ile Gln Gly Met Asn Ser Gln Glu Leu
            20                  25                  30

Asp Gly Arg Asn Ile Thr Val Asn Glu Ala Gln Ser Arg Gly Ser Gly
        35                  40                  45

Gly Gly Gly Gly Gly Gly Tyr Ser Arg Gly Ser Gly Gly Gly
    50                  55                  60

Gly Gly Gly Gly Tyr Ser Arg Gly Gly Gly Gly Gly Tyr Gly Gly
65                  70                  75                  80

Gly Gly Arg Arg Glu Gly Gly Tyr Gly Gly Gly Gly Gly Tyr Asn
                85                  90                  95

Ser Arg Ser Ser Gly Gly
                100

<210> SEQ ID NO 10
<211> LENGTH: 96
<212> TYPE: PRT
<213> ORGANISM: Oryza sativa

<400> SEQUENCE: 10

Lys Pro Thr Gly Arg Ser Gly Val Glu Asp Gln Lys Trp Gly Gly Ala
1               5                   10                  15

His Gly Gly Gly Tyr Gly Tyr Gly Gly Gly Tyr Gly Gly Gly Gly Tyr
            20                  25                  30

Gly His Pro Gly Tyr Gly Gly Gly Tyr Gly Gly Gly Tyr Gly His Pro
        35                  40                  45

Gly Tyr Gly Gly Gly Tyr Gly Gly Gly Tyr Gly Gln Gly Tyr Gly Cys
    50                  55                  60

Gly Tyr Gly His Pro Gly His Ser Gly Gly Tyr Gly Gly Gly Gly Gly
65                  70                  75                  80

Tyr Gly Gly Gly Gly Gly Tyr Gly Gly Gly His Gly Gly Gly Trp Pro
                85                  90                  95
```

PLANT DERIVED ANTIBIOTIC PEPTIDE RICH IN GLYCINE

CROSS-REFERENCE TO RELATED APPLICATION

This application is a National Stage entry of International Application No. PCT/BR2008/000001, filed Jan. 2, 2008, the entire specification claims and drawings of which are incorporated herewith by reference.

SEQUENCE LISTING

The instant application contains a Sequence Listing which has been submitted in ASCII format via EFS-Web and is hereby incorporated by reference in its entirety. Said ASCII copy, created on Apr. 13, 2011, is named 27656023.txt and is 8,235 bytes in size.

FIELD OF THE INVENTION

The present invention relates to a new peptide extracted from the seeds of guava (*Psidium guajava*), possessing bactericide activity, especially against gram-negative bacteria known to cause urinary, hospital and intestinal tract infections, (*Proteus* sp. and *Klebsiella* sp.). The peptide possesses the amino acid sequence RESPSSRMEC YEQAERYGYG GYGGGRYGGG YGSGRGQPVG QGVERSHDDN RNQPR (SEQ ID NO: 1), and belongs to the class of glycine rich proteins with an approximate molecular weight of 5 kDa.

BACKGROUND OF THE INVENTION

The last two decades have seen a significant increase in the bacterial resistance to synthetic antibiotics placed on the market. The gram-negative bacteria of the Enterobacteriaceae family, such as *Klebsiella* sp. and *Proteus* sp., which were formerly susceptible to medicines are currently the main cause of hospital infections in several developing countries (Mendes, 2000). Consequently, an increase in the fatality-rate of immuno-depressed patients infected with these bacteria has been reported. In response to this problem, several compounds of proteic origin having anti-microbial activity have been isolated from different species of plants, mammals and microorganisms (Campos et al., 2006; Bevins, 2006).

Various plant proteins have demonstrated activity against bacteria and fungi (Selitrenikkoff, 2001). They normally have a preponderant role in the plant's defense, protecting it from environmental pathogens. These proteins have been classified within various groups and families in accordance with their structural and functional similarities. These include cyclotides, defensins, γ-thionins, Lipid-Transporting Proteins (LTPs), lectins, digestive enzyme inhibitors and various others (Selitrenikkoff, 2001, Pelegrini and Franco, 2005; Franco et al., 2002; Pelegrini et al., 2006).

Glycine rich proteins (or GRPs) consist of a new group of plant defence molecules described as having anti-microbial activity. They were initially characterised as storage proteins, being used as essential sources of amino acids (Mousavi, 2005). Previous studies have indicated the activity of glycine rich proteins in adapting to cold and in increasing tolerance to low temperatures, functioning as RNA bonding factors (Shinozuka, 2006). Furthermore, it has been demonstrated that the expression of its corresponding mRNA increases in plants exposed to low temperatures (Shinozuka, 2006). Also, it has been noted that glycine rich proteins may alter the germination and growth of plants under stress conditions, such as high salt concentrations or dehydration, (Kwak, 2005). Former studies indicated that eight glycine rich proteins isolated from seeds of *Triticum kiharae* did not demonstrate anti-microbial activity against bacteria but did, however, show activity against filamentous fungi, such as *Helminthosporium sativum* and *Fusarium culmorum* (Egorov, 2005). GRPs may be characterised by their high percentage of glycine residues and their primary sequence but, however, this varies with each plant and organism (Mousavi, 2005). Glycine rich proteins can be classified within three different groups according to their glycine content. The first group contains proteins presenting over 70% glycine residues in the amino acid sequence, such as GRPs of tomato and saltbush (Ringli, 2001). There is also a third group that includes proteins of high glycine content but having no specific domains (Ringli, 2001). The proteins from this group are normally hydrophobic rather than hydrophilic with this trait possibly being caused by the presence of tyrosine and phenylalanine (Ringli, 2001). The secondary structure of GRPs has not been fully studied but preliminary researches report that it may be predominantly β-sheet rich (Matsui, 1995).

Previous researches indicate that genes of glycine rich proteins are mainly found in vascular tissues, more specifically in the xylem (Ryser, 1992; Keller, 1988; Keller, 1989), despite that they have also been found in hypocotyls and pistils (Ye, 1991). The expression of GRP genes seems to be linked to inducement by stress and influenced by ambient changes, such as wounding, hormone treatment, low temperatures and dehydration (Keller, 1988; de Oliveira, 1990; Bergeron, 1994; Keister, 1995; Laberge, 1993; Condit; 1987).

This work had the objective of purifying and characterizing an anti-microbial protein from guava seeds (PgAMP1) similar to glycine rich proteins. This protein proved capable of inhibiting the growth of two gram-negative bacteria, both recognized as causing hospital infections, as well as urinary and gastrointestinal infections. This is the first report of a protein from the group of glycine rich proteins that demonstrates activity against human pathogenic bacteria.

The PgAMP1 protein identified from the present research and object of the present invention proved capable of inhibiting the growth of two gram-negative bacteria (*Proteus* sp. and *Klebsiella* sp.) and the sequence of 55 amino acids allowed its classification as a member of the glycine rich proteins.

The search for prior references disclosed documents describing the anti-bacterial activity of essential oils or extracts (aqueous, hydroalcoholic, ethanolic, methanolic and/or chloroformic) of *Psidium guajava* against different bacteria species (refer to Table 1, below). Different parts of the plant were used to obtain the extracts, mainly the leaves and the bark of the stem. There are no reports of the use of seeds of *P. guajava* for obtaining compounds having anti-bacterial activity.

TABLE 1 micro-organisms and respective reports of anti-bacterial activity in extracts or essential oils of *Psidium guajava*.

| Species | References |
| --- | --- |
| *Actinomyces* sp. | Razak et al. (2006). |
| *Bacillus anthracis* | Akinpelu & Onakoya (2006). |
| *Bacillus cereus* | Akinpelu & Onakoya (2006); Arima & Danno (2002). |
| *Bacillus subtilis* | Akinpelu & Onakoya (2006); Karawya et al. (2001); Martinez et al. (1997); Rabe & van Staden (1997); Sanches et al. (2005). |

TABLE 1-continued micro-organisms and respective reports of anti-bacterial activity in extracts or essential oils of *Psidium guajava*.

| Species | References |
|---|---|
| *Clostridium sporogenes* | Akinpelu & Onakoya (2006). |
| *Corynbacterium pyogenes* | Akinpelu & Onakoya (2006). |
| *Escherichia coli* | Abdelrahim et al. (2002); Akinpelu & Onakoya (2006); Carvalho (2002); Chan et al. (2006); Martinez et al. (1997); Rivera de Leon et al. (2001); Vieira et al. (2001); Voravuthikunchai et al. (2004). |
| *Klebsiella pneumoniae* | Abdelrahim et al. (2002); Akinpelu & Onakoya (2006); Rivera de Leon et al. (2001). |
| *Mycobacterium phlei* | Karawya et al. (2001). |
| *Propionibacterium acnes* | Qadan et al. (2005). |
| *Proteus mirabilis* | Gonçalves et al. (2005); Karawya et al. (2001). |
| *Proteus morganii* | Karawya et al. (2001). |
| *Proteus* spp. | Carvalho (2002); Chan et al. (2006). |
| *Proteus vulgaris* | Abdelrahim et al. (2002); Karawya et al. (2001). |
| *Pseudomonas aeruginosa* | Abdelrahim et al. (2002); Akinpelu & Onakoya (2006); Carvalho (2002); Chah et al. (2006); Gnan & Demello (1999); Martinez et al. (1997); Rivera de Leon et al. (2001). |
| *Pseudomonas fluorescens* | Akinpelu & Onakoya (2006). |
| *Salmonella enteritidis* | Arima & Danno (2002). |
| *Salmonella paratyphi* | Lutterodt et al. (1999). |
| *Salmonella* spp. | Carvalho (2002). |
| *Salmonella typhi* | Lutterodt et al. (1999). |
| *Salmonella typhimurium* | Gnan & Demello (1999); Lutterodt et al. (1999). |
| *Shigella dysenteriae* | Akinpelu & Onakoya (2006); Ali et al. (1997); Ali et al. (1996); Lutterodt et al. (1999). |
| *Shigella flexneri* | Lutterodt et al. (1999). |
| *Shigella sonnei* | Lutterodt et al. (1999). |
| *Shigella* spp | Carvalho (2002); Chah et al. (2006). |
| *Staphylococcus aureus* | Abdelrahim et al. (2002); Akinpelu & Onakoya (2006); Betoni et al. (2006); Chah et al. (2006); Gnan & Demello (1999); Gonçalves et al. (2005); Jaiarj et al. (1999); Lutterodt et al. (1999); Martinez et al. (1997); Nascimento et al. (2000); Qadan et al. (2005); Rabe & van Staden (1997); Rivera de Leon et al. (2001); Sanches et al. (2005); Vieira et al. (2001). |
| *Staphylococcus epidermidis* | Gnan & Demello (1999); Qadan et al. (2005); Rabe & van Staden (1997). |
| *Streptococcus faecalis* | Akinpelu & Onakoya (2006). |
| *Streptococcus mitis* | Razak et al. (2006). |
| *Streptococcus pyogenes* | Gnan & Demello (1999); Gonçalves et al. (2005). |
| *Streptococcus sanguinis* | Razak et al. (2006). |
| *Vibrio cholerae* | Lutterodt et al. (1999). |

The documents encountered when researching antecedents also confirmed that there is no consensus in relation to the species for which the extracts of *P. guajava* showed inhibitory activity. Some studies reported, for example, anti-microbial activity of *P. guajava* on bacteria of the genera *Proteus* (Abdeirahim et al., 2002; Carvalho, 2002; Chah et al., 2006; Gonçalves et al., 2005; Karawya et al., 2001) and *Klebsiella* (Abdelrahim et al., 2002; Akinpelu & Onakoya, 2006; Rivera de Leon et al., 2001), while others (Rabe & van Staden, 1997; Gnan & Demello, 1999; Nascimento et al., 2000) did not identify any activity on these bacteria. Therefore, determination of the composition of the extracts (according with the origin of plant material or the solvents used in the extraction, for example) proved to be an important factor when verifying the anti-bacterial activity of *P. guajava*.

Some of the compounds from the extracts identified as having anti-microbial activity included flavonoids, such as guaijaverin, quercetin (Arima & Danno, 2002 and Rabe & van Staden, 1997), morin-3-O-α-L-Iyxo-pyranoside and morin-3-O-α-L-arabo-pyranoside (Arima & Danno, 2002; JP2004250406); triterpenes, such as α and β-amyrin (Sanches et al., 2005); sesquiterpenes such as caryophylene, aromadendrene, α and β-selinene or β-bisabolene (Karawya et al., 2001); sterols such as β-sitosterol (Sanches et al., 2005) and tannins (Akinpelu & Onakoya, 2006). None of these works, however, describe the peptide PgAMP1 or any other protein rich in glycine derived from *P. guajava*.

The glycine rich proteins are noted for their anti-microbial activity (Egorov et al., 2005; Park et al., 2000; van Kan et al., 2001; CN1699409; CN1699416; EP1693381), but there are nevertheless few studies that relate to a specific action against bacteria (Park et al., 2000; van Kan et al., 2001; EP1693381).

Park et al. (2000) describe two new peptides isolated *Capsella* bursa-pastoris that present inhibitory activity against gram-negative bacteria. Van Kan et al. (2001) describe the action of clavanin A on the bacteria *Micrococcus flavus*.

European patent application EP1693381 describes several sequences of glycine rich proteins that exhibit anti-bacterial activity. The peptides described in this work have molecular weights under 10 kDa and are derived from various organisms ranging from man to (*Saccharomyces cerevisiæ*). Due to their antibiotic activity, the inventors propose the use of these peptides in the prevention and/or treatment of infectious diseases caused by bacteria and, more specifically, in the cases where the pathogenic organisms have developed resistance to the antibiotics commonly prescribed. To confirm the anti-bacterial activity of these sequences, the inventors advanced experiments involving the peptides described and the species *Escherichia coli* and *Bacillus subtilis*.

It should be noted that the present invention represents a technologic advance considering that despite the existence of reports about the anti-bacterial activity of glycine rich proteins, none of these documents describe a peptide that is derived from *P. guajava* or that shows action against the bacteria of genera *Proteus* sp. and *Klebsiella* sp.

SUMMARY OF THE INVENTION

The present invention relates to a new peptide extracted from guava seeds (*Psidium guajava*), possessing bactericide activity, especially against gram-negative bacteria known to cause urinary, hospital and intestinal-tract infections, (*Proteus* sp. and *Klebsiella* sp.). Furthermore, it is emphasised that the amino acid sequence may be identical or functionally equivalent in relation to the natural peptide comprising the primary object of the present invention.

The peptide possesses the amino acid sequence RESPSS-RMEC YEQAERYGYG GYGGGRYGGG YGSGRGQPVG QGVERSHDDN RNQPR (SEQ ID NO: 1), and belongs to the glycine-rich protein class with an approximate molecular weight of 5 kDa.

The present invention also relates to antibiotic compositions for human, veterinary and plant treatment. The compositions should include at least one peptide object of the present invention, as well as a pharmaceutically suitable excipient or agronomically acceptable carrier. Alternatively, the peptide may be used in the transformation of organisms intending resistance to certain pathogens as well as other adaptive advantages, as well a phenotypical characteristics of multiple interest.

BRIEF DESCRIPTION OF THE DRAWINGS

FIG. 3: A) Amino acid sequence of Pg-AMP1 (SEQ ID NO: 1). N- indica the N-terminal and C- indicates the C-terminal. B) Alignment of Pg-AMP1 with other glycine rich proteins from plants (SEQ ID NOS 2-10, respectively, in order of appearance).

DETAILED DESCRIPTION OF INVENTION

Figure 1:
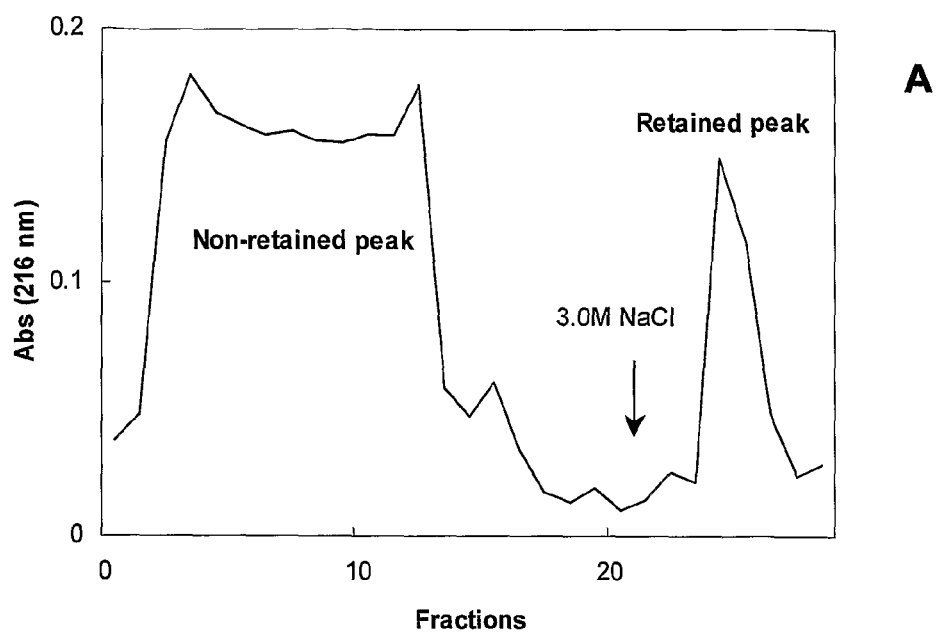
FIG. 1: A) Chromatography in Red-Sepharose CI-6B of the raw extract of guava (*P. guajava*) seed. The black arrow indicates the initial election of the proteins retained using Tris-HCl containing NaCl 3.0 M. B) Profile of the HPLC (Vydac C18-TP) reverse phase chromatography of the fractions retained in the Red-Sepharose generated from the guava (*P. guajava*) seed. The diagonal line indicates the linear acetonitrile gradient. Also, the graph in the right corner represents the re-chromatography of the protein fraction in the same column.
Figure 1:
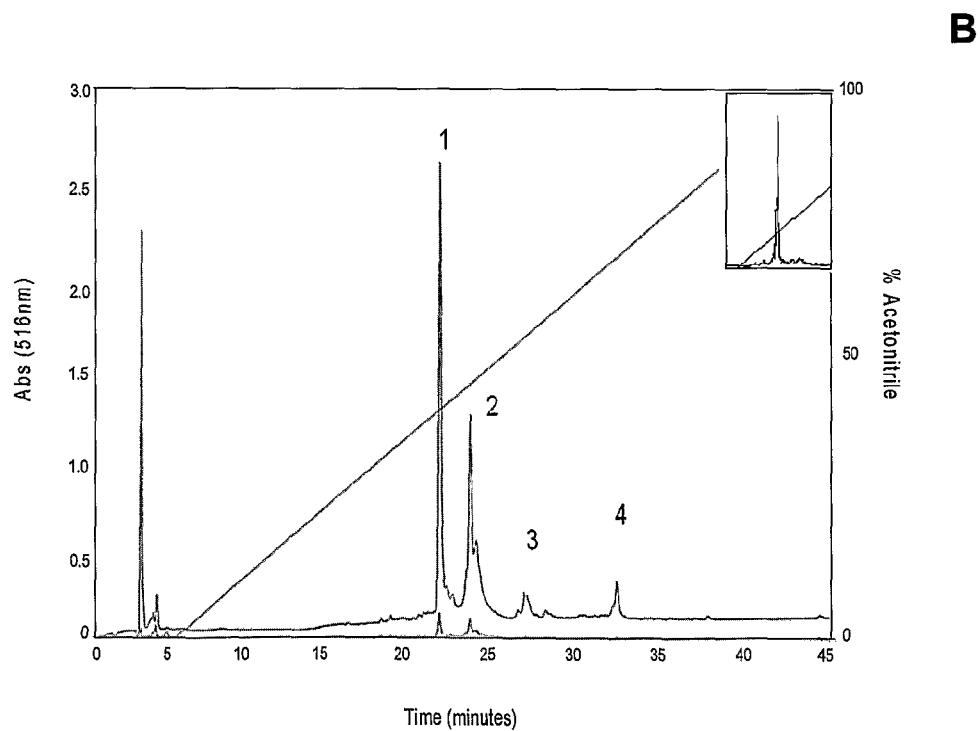

One of the current problems confronted in human health consists in the increased resistance of pathogenic bacteria to the synthetic antibiotics presently marketed. This renders the treatment of several diseases difficult, such as infections of the urinary and gastrointestinal tracts. With the intent of reducing the number of cases of these diseases as well as reducing the rate of bacterial resistance, various studies have been undertaken relating to the action of defence peptides having anti-bacterial activity. In the present project, a protein from the seeds of the guava plant, Pg-AMP1, was purified and characterised biochemically and structurally with the purpose of developing a new strategy against bacteria causing infections of the urinary and gastrointestinal tracts. Furthermore, bio-assays were performed on this protein against the two gram-negative bacteria that are the main causes of the target diseases: *Klebsiella* sp. and *Proteus* sp. The three-dimensional structure of Pg-AMP1 was obtained by means of in silico studies which revealed the dimeric structural formation for anti-bacterial activity. These results allow the development of new antibiotics capable of retarding the process of bacterial resistance and also aid in the treatment of diseases.

Extraction and Isolation of the Proteins from Guava Seeds (*P. guajava*):

The proteins from guava seeds were extracted using a solution of NaCl 0.6 M and HCl 0.1% (1:3 w/v). The raw extract was centrifuged and the supernatant was precipitated with ammonium sulphate (0-100%). After precipitation, the fractions were again centrifuged at 5.000 rpm for 20 minutes at 4° C. The precipitate was resuspended, dialysed against distilled water and placed in a Red-Sepharose affinity column balanced with Tris-HCl 0.15 M pH 7.0 containing $CaCl_2$ 50 mM. The discarded fractions were removed with balancing buffer and the retained fractions were eluted through the addition of balancing buffer augmented with NaCl 3.0 M. After dialysis and freeze-drying, 1.0 mg of the retained fraction was diluted with trifluoracetic acid 0.1% and placed in a HPLC (Vydac C-18TP) reverse phase chromatography column, where the proteins were eluted with a linear gradient of acetonitrile (0-100%).

Molecular Weight Analysis:

The molecular mass of the proteins obtained by HPLC was analysed by SDS-PAGE according to the method of Laemmli et al. (1970) with modifications. The molecular weight analysis was performed with polyacrylamide gel 5%. The samples were submitted to 200 volts for a period of 45 minutes and tinted with silver nitrate. The HPLC samples were analysed with MALDI-TOF (Voyager-DE STR Bioworstations), according to the method of Franco et al. (2000). The freeze-dried proteins were diluted with trifluoracetic acid 0.1% and applied to a matrix composed of sinapic acid (acetonitrile/trifluoracetic acid 0.1% 1:1 v/v). This solution was homogenised and placed in MALDI-TOF equipment. The ions were eliminated by laser radiation at 337 nm, and accelerated to a power of 23 kV. The samples were then ionised with 100-200 bursts by a 3-ns laser pulse. The signal was assessed in a fraction of 500 MHz and the data was shown by a Voyager standard system.

Amino Aid Sequencing:

The samples obtained from the HPLC were freeze-dried with the purpose of removing the acetonitrile and the trifluoracetic acid. The protein sequence was ascertained using MS analysis as described by Wang et al, (2000) with modifications. The protein samples were incubated with trypsin 10 μg/ml in Tris-HCl 2.5 mM for 24 hours at 37° C. The tryptic fragments were then eluted in acetonitrile 50% and trifluoracetic acid 0.5% by diffusion facilitated by ultra-sonication. The freeze-dried fractions were dissolved in nanopure water, mixed in a saturated solution of a matrix comprised of alpha-cyano-4-hydroxycinnamic (1:3), deposited on a 600 mm Anchorchip type plaque and left to dry at room temperature. The molecular components had their exact molecular masses determined using a MALDI-TOF/TOF UltraFlex II (Bruker Daltonics, Germany) mass spectrometer. The spectrums were obtained in a delayed reflection extraction mode under a mass varying between 1.000-20.000 Da. Spectrums of 64 bursts at 20 different positions were continuous in order to provide a "fingerprint" of protein mass for the sample. The ions of the proteins generated by autolysis of the trypsin were used as internal standard models for calibrating the spectrum mass. The masses of the proteins were analysed by the Ms-Fit software, based on the following parameters: mass tolerance of 0.5 Da, minimum of four peptide combinations and no cleaving errors. External calibration was used in reflected and positive operation mode. Ions that presented an appropriate signal-sound ratio were submitted to fragmentation (MS/MS) in LIFT operation mode. Isoforms found for any protein were analysed by the FindMod and Peptide Mass in ExPaSy to predict their possible modifications. Sequence homology was done using the BioEdit and FASTA3 softwares.

'In Silico' Analysis:

The amino acid sequence obtained was compared with other proteins in the NCBI Protein Data Bank (www.ncbi.nih.gov). An alignment using ClustalW (Thompson, 1994) and BioEdit (Page, 1996) softwares was used for the protein with the purpose of analysing primary sequence similarities within the group of glycine rich proteins. A phylogenetic tree was also prepared using the guava protein with other proteins that showed greater identity by means of the TreeView (Hall, 1999) software Molecular Modelling:

A comparative alignment was performed with the protein structure database in order to elucidate the 3D structure of AMP-PgGRP. For such, the Bionfo Meta Server (Ginalski et al., 2003) was used but this did not disclose any similar structure. Therefore, protein structure prediction techniques were carried out ab initio. For such, the Gromacs (Lindahl et al., 2001) molecular dynamics package was used. A primary structure was initially constructed using the DeepView Swiss PDB Viewer (Guex et al., 1997) software. This structure was then placed in a cubic box, centralised and filled with molecules of water. A partial energy minimisation simulation was executed using 2000 stages of Steepest Descent with the intent of removing possible stereochemical impediments. This was followed by a complete simulation using a coupling temperature and pressure of 300 k and 1 atm, respectively, and Newton's (MD) movement equations as dynamic method at 60000 picoseconds. The entire simulation was executed at a bi-processed Sun AMD Opteron workstation. The trajectory and final model was visualised using the Pymol (DeLano, 2002) software.

Bioassays Against Bacteria:

The bioassays against bacteria were performed using 1.0 ml of Luria Bertani medium (NaCl 10 g.l$^{-1}$, yeast extract 5 g.l$^{-1}$ and bactopeptone 45 g.l$^{-1}$). Two species, namely *Klebsiella* sp. and *Proteus* sp., were used, with the protein under test was restricted to micromolar concentrations. The bacteria grew in the LB medium during 16-18 hours at 37° C. before being evaluated with the proteins. Distilled water was used as negative control and chloramphenicol 40 µg.ml$^{-1}$ as positive control. Protein from guava seeds was incubated against the bacteria at 37° C. for 4 hours. Bacterial growth was assessed by an absorbance reading at 600 nm at each hour of the experiment. Each experiment was performed in triplicate.

Results and Discussion:

a) Purification and Molecular Characterization of PgAMP1

Figures 2, 3A:
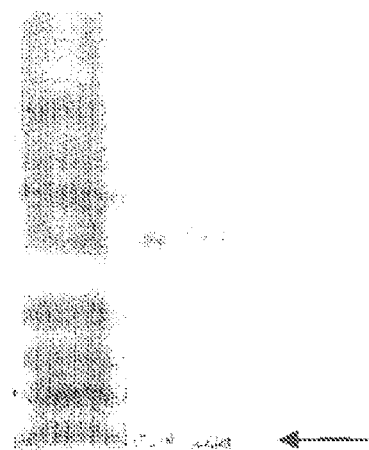
FIG. 2: SDS-PAGE of Pg-AMP1 (line 2, arrow). Line 1 corresponds to molecular marker.

A fraction of guava seed (*Psidium guajava*) precipitated with ammonium sulphate (0-100%) was placed in a CI-6B Red-Sepharose affinity column with the purpose of isolating anti-microbial peptides, which resulted in a retained peak (FIG. 1A). This retained peak showed several proteins when analysed by SDS-PAGE, since the molecular masses observed varied between 5.0 and 80.0 kDa (data not shown). Samples of the retained peak were then submitted to reverse phase chromatography (HPLC), which revealed a majority peak of 42% acetonitrile (FIG. 1B). Samples from this peak were again submitted to chromatography using a 20-50% acetonitrile gradient which disclosed a purified peptide in 42% of acetonitrile (data not shown). Following chromatography, the samples of the peak from the HPLC were submitted to molecular mass analysis by SDS-PAGE and showed a peptide with a molecular mass under 10 kDa (FIG. 2).

b) Amino Acid Sequencing and Alignment:

Complete sequencing of the guava protein revealed a fragment of 55 amino acid residues (FIG. 3A). An alignment using the FASTA3 software showed that the sequence obtained presented a 72% similarity with glycine rich proteins. A comparison of the primary sequence of Pg-AMP1 with nine other glycine rich proteins isolated from plants was performed using the BioEdit (Hall, 1999) software. It can be seen that despite the primary sequence among glycine rich proteins generally being very diverse, they do show a conserved region where glycine residues predominate (FIG. 3B). However, PgAMP1 seems to belong to the third group of GRPs, since it exhibits a high content of glycine residues, but does not contain any specific domain, as seen in the proteins of *P. pattens, B. napus, S. tuberosum, M. sativa, R. obtusifolius* and *E. esula* (Hovarth and Olson, 1998; Kevei et al., 2002; Vermel et al., 2002). It may further be perceived that positively charged residues found in the middle of the region rich in glycine seem to be conserved in this group of proteins, such as Arg35 and Arg45 (FIG. 3B). Interestingly, the presence of cysteine residues and the formation of disulphate bonds are not conserved among the glycine rich proteins (Fujimura et al., 2003).

The sequencing of Pg-AMP1 revealed a fragment of 55 amino acid residues with similarities to the glycine rich proteins (FIG. 3A). This is a broad and varied family of proteins having different amino acid sequences and functions. Its main characteristic lies in possessing over 60% of its primary sequence constituted of glycine residues but being able to be classified in three distinct groups according to the presence/absence of other conserved domains (Mousavi, 2005; Ringli, 2001). Nevertheless, various glycine rich proteins have been described in the literature and shown diverse functions in plants. Some authors report glycine rich proteins acting as post-transcriptional regulators under conditions of stress and, consequently, in the expression of genes in various plant species (Kim, 2005). Glycine rich proteins acting as RNA bonding molecules have also been described in plants such as rice (Nomata, 2004; Lee, 1997). Furthermore, certain of the proteins from this group isolated from wheat were recently described as anti-microbial proteins acting against filamentous fungi (Egorov, 2005).

An alignment of Pg-AMP1 with nine other glycine rich proteins demonstrated that despite the primary sequence differing broadly in this group, there is nevertheless similarity in glycine rich domain (FIG. 3B). A pattern of conservation may also be perceived with certain tyrosine residues which suggest that this fragment may be important to its structure and/or function. A positively charged residue may also be noted in the middle of the glycine rich region with conservation in the other proteins present in the alignment. The role of these residues have not yet been fully explained experimentally, but there are indications that they may be important to the stability of the proteins from this family.

Furthermore, the significant increase in the bacterial resistance rates to synthetic antibiotics has made the treatment of urinary, hospital and gastrointestinal infections much harder. With this intent, Pg-AMP1 was tested against gram-negative bacteria of the genera *Klebsiella* sp. and *Proteus* sp., both being the main causes of infection in immunocompromised patients in developing countries. As such, Pg-AMP1 demonstrated an inhibitory activity of 90% and 30%, respectively for these bacteria. Nevertheless, Pg-AMP1 seems to be the first glycine rich protein from plants to exhibit anti-microbial activity against gram-negative bacteria pathological to humans.

c) Bioassays Against Gram-Negative Bacteria

Figure 4:
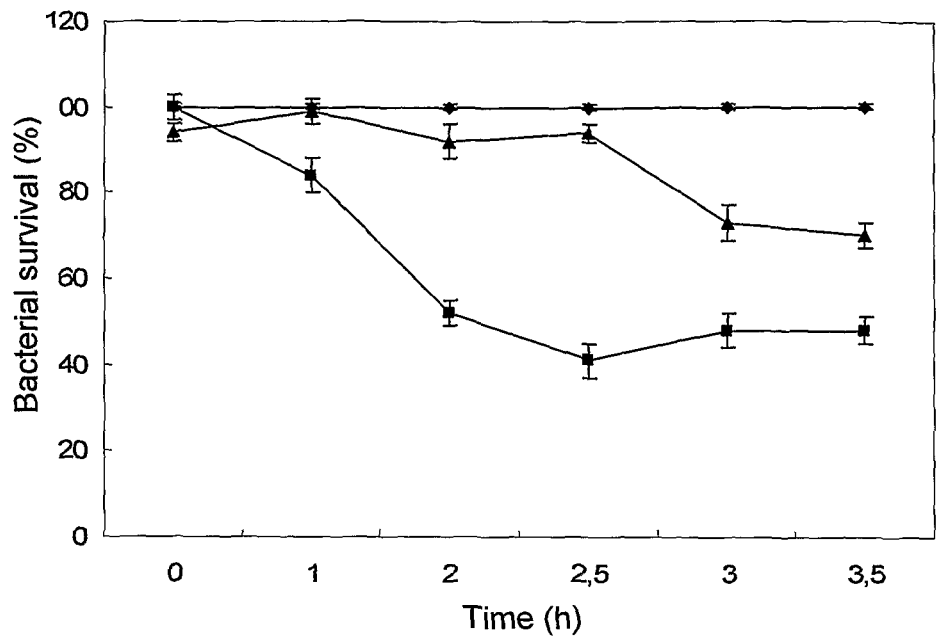
FIG. 4: Bacterial bio-assay using purified Pg-AMP1 against A) *Proteus* sp. and B) *Klebsiella* sp. (■) indicates negative control, (▲) indicates positive control and (♦) indicates trial using Pg-AMP1.
Figure 4:
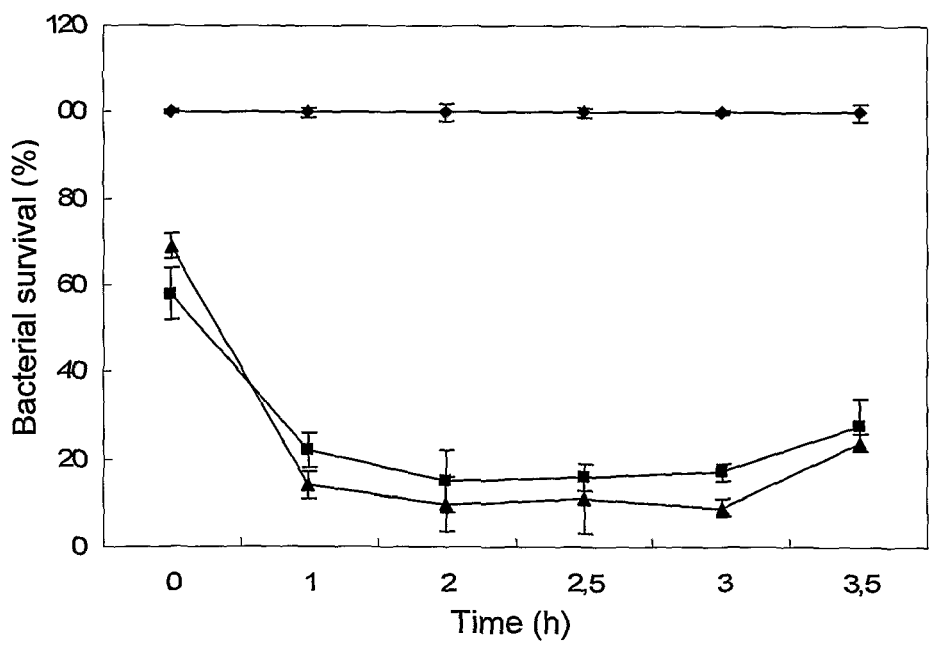

Purified Pg-AMP1 was used for in vivo bioassays against gram-negative bacteria. This protein proved harmful against *Klebsiella* sp. and *Proteus* sp., demonstrating an inhibitory activity of 90% and 30%, respectively, for these bacteria, in micromolar concentrations (FIGS. 4A e 4B). Pg-AMP1 also proved specific against gram-negative bacteria since preliminary bioassays against gram-positive bacteria, such as *Staphylococcus aureus*, did not reveal any inhibitory activity. There are few reports in the literature of glycine rich proteins having anti-microbial activity. In this manner, it was observed that a RNA bonding protein rich in glycine isolated from *Nicotiana glutinosa* may be related to the plant-pathogen relationship since the expression of its gene increased when the plant was infected with the TMV virus (Naqvi et al, 1998). Another glycine rich protein, in this case isolated from the pumpkin and called 'curcumoschina', exhibited anti-fungic activity against *Botrytis cinerea, Fusarium oxysporum* and *Mycosphaerella oxysporum* (Wang et al., 2003). Furthermore, certain glycine rich proteins presented a binding domain to chitin which rendered them capable of inhibiting the growth of filamentous fungi, such as in the case of two proteins isolated from oats (*Avena sativa*) and *Ginkgo biloba* (Huang et al., 2000; Lii e Claeson, 2003). Nevertheless, there are no accounts of a glycin rich protein isolated from plants presenting activity against bacteria. Therefore, this is the first time that a glycine rich protein from a plant presents anti-microbial activity against gram-negative bacteria pathogenic to humans.

d) Molecular Modelling

Figure 5:
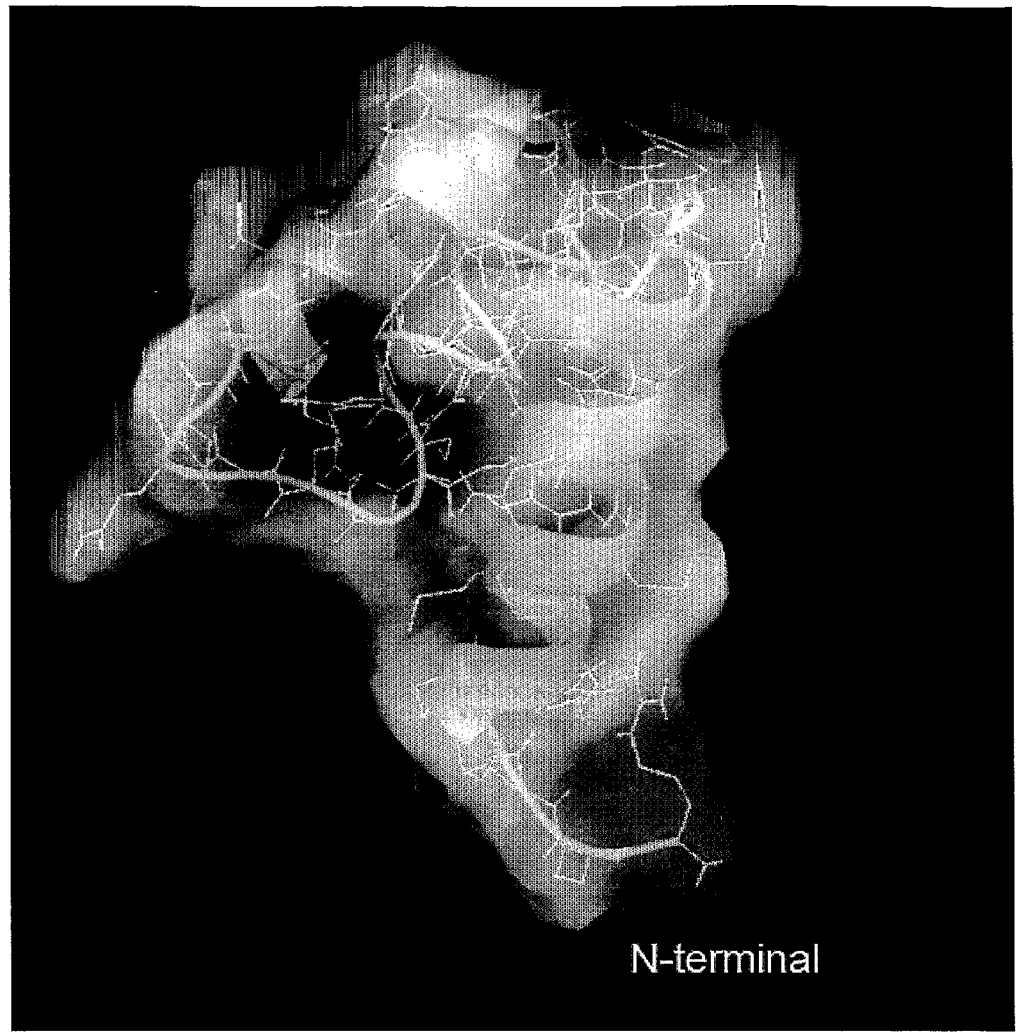
FIG. 5: Cartoon form representation of AMP-PgGRP. The electrostatic layer is represented in blue for positive charges, in red for negative charges and white for non-polars. Red spirals represent α-helixes and green tubes represent loops. The lateral chain is represented by green lines.
Figure 6:
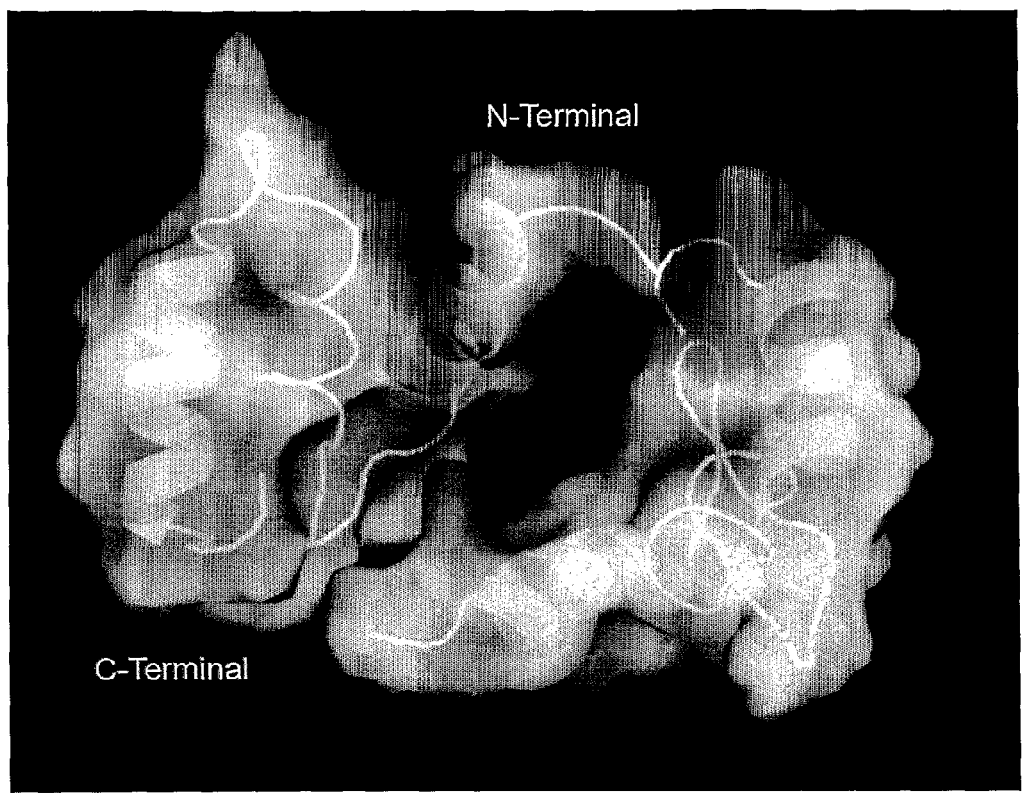
FIG. 6: Representation of AMP-PgGRP by dimerism. The electrostatic layer is represented in blue for positive charges, in red for negative charges and white for non-polars. Red spirals represent α-helixes and green tubes represent loops.

The final model is composed of two α-helixes, with one at the n-terminal and the other at the c-terminal, with a loop spiraling between them (FIG. 1). It is this loop that contains the majority of glycine residues conferring its flexibility. The α-helix extremities have arginine residues conferring a positive charge at these sites (FIG. 1). Several non-polar residues are located along the structure and serve to provide molecular hydrophobicity (FIG. 5). Analysis of the electro-static layer shows two large charged regions, one positively at the n-terminal and another negatively the length of the c-terminal (FIGS. 5 and 6). These areas allowed two AMP-PgGRP to aggregate and form dimeric molecules (FIG. 6). A possible mechanism in the action of these peptides may be the contact of the arginine at the 'N' and 'C' terminals with the phospho-lipid heads of the plasmatic membranes of the bacteria resulting in the rupture of the membrane thus allowing an osmotic unbalance and, consequently, the occurrence of cellular lysis (Shai et al., 2001). Another mechanism could be the agglomeration of various peptides through hydrophobic forces which would form a carpet stretching the bacterial membranes thus hindering their necessary flexibility and destroying their structure (Shai et al., 2001). Experiments with nuclear magnetic resonance and molecular dynamics may soon take place so as to provide a better understanding of the method of action.

The present invention, namely a new protein capable of inhibiting the growth of gram-negative bacteria may, in the near future, provide new information concerning the mechanisms of action of this group of proteins. Furthermore, antibacterial proteins from seeds of the guava plant may furnish the new tools for the control of pathogens, through genetic engineering, especially in the case of plants and animals.

What is claimed is:

1. An isolated antibiotic glycine rich peptide with antimicrobial activity against Gram-negative bacteria, comprising: the identical amino acid sequence or an amino acid sequence showing at least 72% similarity and at least the same antimicrobial activity as that of the peptide sequence set forth below: RESPSSRMEC YEQAERYGYG GYGGGRYGGG YGSGRGQPVG QGVERSHDDN RNQPR (SEQ ID NO: 1).

2. Antibiotic peptide of claim 1, wherein the full length peptide chain or parts thereof comprise the amino acids α-D and/or α-L.

3. Composition for inhibiting the development of a target cell, comprising: (a) at least one antibiotic peptide according to claim 1, (b) optionally one or more antibiotic peptides having antimicrobial activity; and (c) a suitable pharmaceutical excipient.

4. The composition of claim 3, wherein said composition is suitable for human, veterinary or pharmaceutical uses.

5. Composition for detaining phytopathogens and for protecting plants against pathogens, comprising: (a) at least one antibiotic peptide according to claim 1, and (b) an agronomically acceptable carrier.

* * * * *